(12) United States Patent
Liu et al.

(10) Patent No.: US 7,777,635 B2
(45) Date of Patent: Aug. 17, 2010

(54) POWER FAILURE MANAGEMENT FOR RESPIRATORY SYSTEM HEATER UNIT

(75) Inventors: Zhan Liu, Fremont, CA (US); Ashok Mahadevan, Alpharetta, GA (US); Robert L. Snyder, Suwanee, GA (US)

(73) Assignee: Smiths Medical ASD, Inc., Rockland, MA (US)

( * ) Notice: Subject to any disclaimer, the term of this patent is extended or adjusted under 35 U.S.C. 154(b) by 196 days.

(21) Appl. No.: 11/927,068

(22) Filed: Oct. 29, 2007

(65) Prior Publication Data
US 2009/0113238 A1 Apr. 30, 2009

(51) Int. Cl.
*G08B 21/00* (2006.01)
(52) U.S. Cl. .............. 340/640; 340/657; 340/635; 340/687; 128/201.13; 128/203.17; 128/204.17
(58) Field of Classification Search .............. 340/455, 340/635, 636.1, 657–664, 693.3, 687, 693, 340/640; 714/5, 10, 14, 22, 24; 128/201.13, 128/203.17, 204.17
See application file for complete search history.

(56) References Cited

U.S. PATENT DOCUMENTS

| | | | | |
|---|---|---|---|---|
| 4,523,295 A * | 6/1985 | Zato | ............... | 714/22 |
| 4,564,748 A | 1/1986 | Gupton | | |
| 4,621,632 A | 11/1986 | Bartels et al. | | |
| 5,082,173 A * | 1/1992 | Poehlman et al. | ............... | 236/11 |
| 5,452,714 A * | 9/1995 | Anderson et al. | ...... | 128/205.11 |
| 5,558,084 A | 9/1996 | Daniel et al. | | |
| 5,943,473 A | 8/1999 | Levine | | |
| 6,078,730 A | 6/2000 | Huddart et al. | | |
| 6,272,933 B1 | 8/2001 | Gradon et al. | | |
| 6,329,796 B1 * | 12/2001 | Popescu | ............... | 320/134 |
| 6,349,722 B1 | 2/2002 | Gradon et al. | | |
| 6,390,091 B1 * | 5/2002 | Banner et al. | ............... | 128/204.21 |
| 6,392,555 B1 * | 5/2002 | Most, Jr. | ............... | 340/664 |
| 6,455,820 B2 | 9/2002 | Bradenbaugh | | |
| 6,557,551 B2 * | 5/2003 | Nitta | ............... | 128/203.17 |
| 6,584,972 B2 | 7/2003 | McPhee | | |
| 6,694,974 B1 | 2/2004 | George-Gradon et al. | | |
| 6,802,314 B2 | 10/2004 | McPhee | | |
| 6,807,965 B1 * | 10/2004 | Hickle | ............... | 128/204.23 |

(Continued)

OTHER PUBLICATIONS

Manual for Fisher & Paykel Model Nos. MR700, MR720, MR730 Respiratory Humidifiers (Mar. 1998) (48 pages).

(Continued)

*Primary Examiner*—Daniel Wu
*Assistant Examiner*—Son M Tang
(74) *Attorney, Agent, or Firm*—Wood, Herron & Evans, LLP

(57) ABSTRACT

A heater unit includes power failure management to detect disruptions in the electrical power supply, such as the AC supply, for the unit. The heater unit emits an audible alarm in response to detection of such a disruption, and may shut down the heater(s) and visuals display(s). The heater unit advantageously includes a power storage device, such as a supercapacitor, to temporarily power the electronic circuitry of the heater unit. Operating parameters, such as of a processor of the electronic circuitry, may be stored in a non-volatile memory response to the disruption, and recalled if the disruption terminates before the level of power has gotten too low to sustain reliable operation of the processor.

29 Claims, 3 Drawing Sheets

U.S. PATENT DOCUMENTS

| | | |
|---|---|---|
| 6,918,389 B2 | 7/2005 | Seakins et al. |
| 6,988,497 B2 | 1/2006 | Levine |
| 7,066,902 B1 * | 6/2006 | Ott et al. .................. 604/23 |
| 7,252,088 B1 * | 8/2007 | Nieves-Ramirez ..... 128/204.18 |
| 7,314,046 B2 * | 1/2008 | Schroeder et al. ...... 128/200.14 |
| 7,495,355 B2 * | 2/2009 | Oberle et al. ................. 307/19 |
| 2002/0129815 A1 | 9/2002 | McPhee |
| 2002/0139367 A1 | 10/2002 | McPhee |
| 2004/0060558 A1 | 4/2004 | Gradon et al. |
| 2004/0079370 A1 | 4/2004 | Gradon et al. |
| 2008/0054497 A1 | 3/2008 | Bradley et al. |
| 2008/0054500 A1 | 3/2008 | Bradley et al. |

OTHER PUBLICATIONS

Technical Manual Fisher & Paykel Respiratory Humidifier Model Nos. MR700, MR720, MR730, MR 480 (Mar. 2001) (64 pages).

Allegiance Healthcare 510K No. K993833 for Airlife® Heated Ventilator and Anesthesia Breathing Circuits (5 pages) (Dec. 10, 1999).

Operating Manual for Fisher & Paykel Model Nos. MR700, MR720, MR730 Respiratory Humidifiers (Mar. 1994) (46 pages).

Instruction Sheet for Airlife® Single Heated Adult Respiratory Circuit (2 pages) (date uncertain).

Cardinal Health RT110 Data for Circuits, reprinted from the internet Jun. 3, 2006 (2 pages).

Fisher & Paykel Airway Temperature Probes Instructions for Use (3 pages) (2003).

* cited by examiner

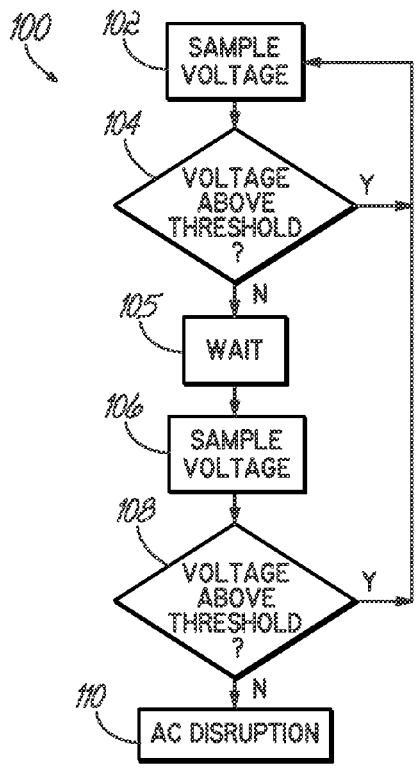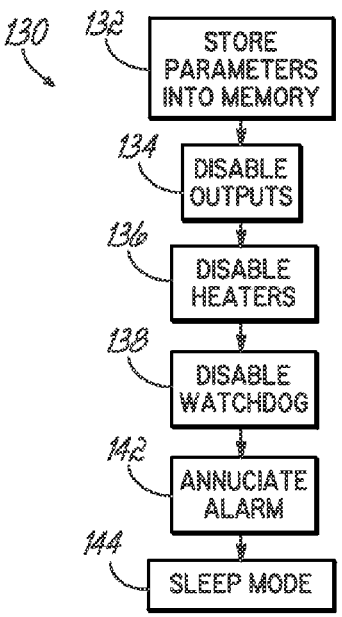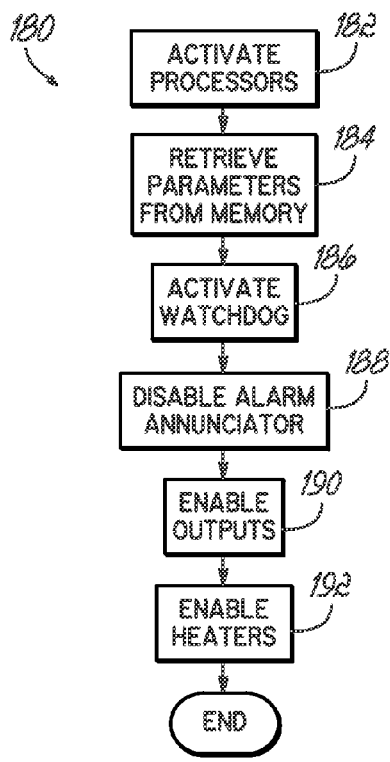

POWER FAILURE MANAGEMENT FOR RESPIRATORY SYSTEM HEATER UNIT

FIELD OF THE INVENTION

The present invention relates to heater units for respiratory systems, and more particularly to power failure management of such heater units.

BACKGROUND OF THE INVENTION

Respiratory systems provide breathable gas, such as oxygen, anesthetic gas and/or air directly to a patient's mouth, nose or airway to assist or facilitate breathing by the patient. A ventilator may be used as part of the respiratory system to drive the breathable gas to the patient through an inspiratory limb hose or conduit of a breathing circuit. The breathing circuit may also include an expiratory limb hose or conduit to carry expelled air and other gas(es) from the patient back to the ventilator.

It is typically desired to warm and impart humidity to the breathable gas before it is provided to the patient. For that purpose, many respiratory systems include a humidification system having a heater unit and a disposable water chamber adapted to be heated by the heater unit. The heater unit supports a heater, such as a hot plate heater which may be comprised of one or more heating elements and a metal plate defining a hot plate. A wall of the chamber, such as the bottom surface thereof, is thermally conductive. The chamber is removably supported on the heater unit with the bottom surface in thermal contact with the hot plate of the heater unit to thus heat the water in the chamber. The breathable gas is coupled to the chamber and is passed through the chamber to be heated and humidified. Examples of heater units, chambers and vented water supplies are shown in U.S. Pat. Nos. 6,988,497 and 5,943,473; and co-pending U.S. patent application Ser. Nos. 11/469,086 and 11/469,113, both filed Aug. 31, 2006.

The inspiratory limb carries the heated and humidified gas to the patient and the expiratory limb, if present, carries exhaled air and possibly other gases from the patient. The hoses or conduits of the inspiratory and expiratory limbs may each be provided with a heater, referred to as a heater circuit, to add heat to the gas passing through the limb and to avoid the incidence of potentially dangerous or hazardous rainout of condensation from the gas(es) passing through the limb. The heater circuit may be in the form of one or more elongated, and possibly coiled, heater wires running along the limb, such as through the interior of the limb. An example of a breathing circuit with heated limbs is shown in U.S. Pat. No. 6,078,730.

The heater unit typically houses the necessary electrical and electronic components to regulate the temperature of the hot plate, as well as heating circuits, if present, of the inspiratory and/or expiratory limbs of the breathing circuit. Power to the heater unit can be disrupted in many ways, including due to problems with the electrical supply lines which is typically an AC supply, power outages or brownouts, AC voltage level drop-outs, or disconnection such as if the power cord used to plug the heater unit into the wall comes away from the heater unit or the wall plug. In some situations, power disruptions may go unnoticed yet can have serious adverse consequences to the patient. Moreover, with some of the complex electronics involved in some heater units, even otherwise minor power disruptions may lead to serious consequences if they are left unattended.

SUMMARY OF THE INVENTION

The present invention provides a heater unit adapted to overcome drawbacks which might otherwise result from power disruptions. To that end, and in accordance with the principles of the present invention, the heater unit is adapted to monitor for power disruptions, and to provide an alarm to warn thereof so that corrective measures can be taken as necessary to protect the patient. In particular, the source of electrical supply is monitored, such as by monitoring an unregulated and filtered DC voltage derived from the source if it is an AC source of power to which the heater unit is connected (or supposed to be connected). If the AC supply is disrupted, that DC voltage will fall below a level indicative of normally sufficient AC supply levels, in response to which the alarm is sounded. The heater unit may be advantageously adapted to also shut off power to the heater components so as to preserve power for a limited period of time sufficient to provide the alarm. In that regard, a power storage device, such as a super-capacitor, may be included in the heater unit to provide a temporary level of operating power in the event of a power disruption.

Further advantageously, the heater unit may continue to monitor for restoration of the power such that if the disruption is terminated, and the AC supply is restored before the super-capacitor has discharged to a level too low for reliable operation of the heater unit, operation of the heater unit may be restored. To that end, in one embodiment, when a power disruption is detected, the current operating parameters of the heater unit may be stored in a non-volatile memory. If the disruption is terminated before the super-capacitor discharges, the parameters may be recalled from the memory and operations resumed based thereon.

The heater unit may include a processor adapted to monitor for power disruptions. The processor normally consumes significant power in its own right while operating to manage the functions of the heater unit. In response to detection of a power disruption, the processor is adapted to enter into a low-power, sleep mode during which the power is monitored but other significant power-consuming activities of the heater unit, such as operation of the heaters or displays, are suspended. When power is detected as having been restored, the processor may power back up into its normal mode ready to resume normal operations of the heater unit after the operating parameters have been reset or restored, either by an operator or automatically if so equipped. Further, should the processor detect in the sleep mode that power is failing altogether, all operations of the heater unit may be suspended and the processor completely shut-down.

The power supply of the heater unit may include a regulator to provide regulated DC voltage for operation of the electronics in the heater unit. The power storage device is coupled to the regulated DC voltage line to provide operating DC voltage for a period of time after the onset of the power disruption. The processor may monitor the power storage device output to determine whether power is failing altogether, such as by detecting that the output from the power storage device has fallen below a minimum threshold below which operation of the processor may become erratic. Should that occur, the processor is completely shut down and may need to be restarted anew when power is restored.

By virtue of the foregoing, there is thus provided a heater unit adapted to overcome drawbacks which might otherwise result from power disruptions. These and other objectives and advantages of the present invention will be more readily apparent from the following detailed description of the drawings.

BRIEF DESCRIPTION OF THE DRAWINGS

The accompanying drawings, which are incorporated in and constitute a part of this specification, illustrate embodiments of the invention and, together with the general description of the invention given above and the detailed description of the embodiments below, serve to explain the principles of the present invention.

FIG. 2 is flowchart illustrating an exemplary AC disruption detection process in accordance with the principles of the present invention and which may be implemented by the processor of the heater unit of FIG. 1

FIG. 4 is a flowchart illustrating an exemplary power down process in accordance with the principles of the present invention and which may be implement by the processor of the heater unit of FIG. 1; and FIG. 5 is a flowchart illustrating an exemplary reactivation sequence in response to termination of the AC disruption in accordance with the principles of the present invention and which may be implemented by the processor of the heater unit of FIG. 1.

DETAILED DESCRIPTION OF DRAWINGS

Figure 1:
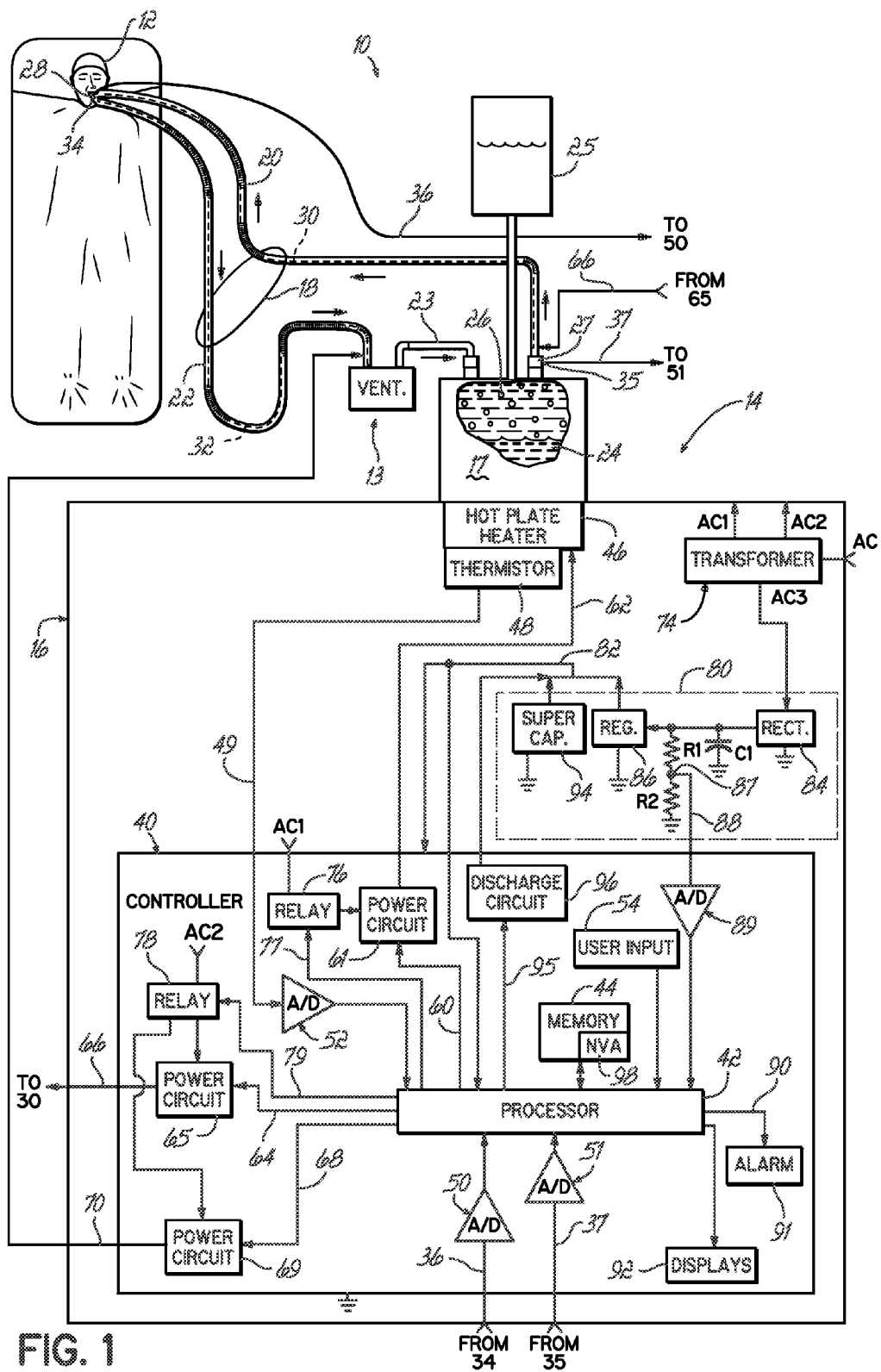
FIG. 1 is a diagram of a respiratory system showing a heater unit adapted to respond to AC disruptions in accordance with the principles of the present invention.

FIG. 1 is an exemplary respiratory system 10 for supplying breathable gases to a patient 12. In the illustrated embodiment, respiratory system 10 includes a ventilator 13 and a humidification system 14 having a heater unit 16 constructed in accordance with the principles of the present invention, a heatable container for water such as a disposable chamber 17, and a breathing circuit 18. Breathing circuit 18 may have a first elongated hose or conduit defining an inspiratory limb 20 and a second elongated hose or conduit defining an expiratory limb 22. Ventilator 13 drives breathable gas, such as oxygen, anesthetic gas and/or air, through gas conduit 23 and into an air inlet of chamber 17. Water 24 is received in chamber 17, either by being poured in manually or automatically from a water supply 25 such as a bag or bottle, and which may be vented. Chamber 17 is heated by heater unit 16 to heat up the water 24 therein. Heated water vapor 26 may also be produced within chamber 17 above the level of water 24 therein. The gas from conduit 23 passes over or through the heated water 24 and/or through heated water vapor 26 to become heated and humidified before exiting the chamber 17 as heated and humidified gas.

The heated and humidified gas flows from chamber 17 to the patient 12 by passing through inspiratory limb 20. A first end of inspiratory limb 20 is coupled to chamber 17 by a connecting member or joint 27, and a second end of inspiratory limb 20 is coupled to a breathing attachment 28 that facilitates delivery of the gas passed therethrough to the patient 12. The breathing attachment 28 may couple to an invasive apparatus such as an endotracheal tube, or a non-invasive apparatus such as a mask (both not shown) that promotes gas delivery. The gas may be further heated while passing through inspiratory limb 20 to breathing attachment 28 by a heater 30, referred to as a heater circuit, associated with inspiratory limb 20. Expiratory limb 22 allows exhaled air and other gas expelled from patient 12 to pass back to ventilator 13. Another heater 32, also referred to as a heater circuit, may be associated with expiratory limb 22 for heating the expelled gas. Heater circuits 30 and 32 may each be comprised of one or more elongated, coiled heater wires extending along or through limbs 20 and 22, respectively, although different types of heater circuits or wire configurations could be employed.

Heater unit 16 may be provided with temperature readings of the gas(es) at breathing attachment 28 and joint 27 via probes 34, 35 respectively coupled thereto and each containing a temperature responsive devices such as thermistor. The temperature readings are coupled over respective communication cables 36, 37. Further details of suitable cables 36, 37 and probes 34, 35 are set out in concurrently-filed U.S. patent application Ser. No. 11/927,020 and concurrently-filed U.S. patent application Ser. No. 11/927,077 the disclosures of both of which are incorporated herein in their entirety by reference.

Heater unit 16 includes a controller 40 having a processor 42 and at least one memory 44, and a heater 46 in the form of a hot plate heater. An example of one suitable heater 46 is described in concurrently filed U.S. patent application Ser. No. 11/926,982 the disclosure of which is incorporated herein by reference in its entirety. Thermally coupled to heater 46 is a temperature responsive device such as a thermistor 48 to provide temperature readings from the hot plate (not shown) of heater 46 as at 49. The temperature readings from probes 34 and 35 and thermistor 48 are analog signals converted to digital signals via respective A/D converters 50, 51, 52 and for use by processor 42 in accordance with the operating parameters in memory 44 (whether pres-stored or loaded therein such as via a user input 54 or otherwise) to control the functions of heater unit 16, including regulating the temperature of heater 46 and heater circuits 30, 32. To that end, processor 42 outputs heater control signals as at 60 to control a power circuit 61 to selectively electrically energize heater 46, as at 62, for regulating the temperature thereof so as to control heating of water 24 in chamber 17 and, if a heated breathing circuit 18 is present, inspiratory control signals as at 64 to control a power circuit 65 to selectively electrically energize heating circuit 30, as at 66, for regulating the heat input to gas passing through inspiratory limb 20 and/or expiratory control signals as at 68 to control a power circuit 69 to selectively electrically energize heating circuit 32, as at 70, for regulating the heat input to gas(es) passing through expiratory limb 22, all as described in greater detail in concurrently-filed U.S. patent application Ser. No. 11/926,990; U.S. patent application Ser. No. 11/927,000; U.S. patent application Ser. No. 11/927,004; and U.S. patent application Ser. No. 11/927,013; the disclosures of all four of which are incorporated herein by reference in their respective entirety.

Heater unit 16 includes a transformer 74 adapted to be coupled, such as via a power cord (not shown), to an AC supply. Transformer 74 includes one or more power taps AC1, AC2 and AC3. Power circuit 61 is coupled through relay 76 to power tap AC1 (or to the AC supply for the input of transformer 74) so as to selectively provide sufficient power (such as from 110 VAC) to heater 46. Processor 42 outputs a power control signal 77 which normally causes relay 76 to be in a state to couple AC power to power circuit 61 such that heater 46 is selectively energized in response to control signal 66. Similarly, power circuits 65 and 69 are coupled through relay 78 to power tap AC2 to selectively provide AC power, such as from 22 VAC, to heater circuits 30 and 32, respectively. Processor 42 outputs a power control signal 79 which normally causes relay 78 to be in a state to couple AC power to power circuits 65 and 69 such that heater circuits 30 and 32 are selectively energized in response to respective control signals 64 and 68.

Heater unit 16 also includes a power supply 80 coupled such as to tap AC3 of transformer 74, to provide a regulated DC voltage supply as at 82 by which to power the electronic components of controller 40. The regulated DC voltage is typically set for the specific electronic components utilized in controller 40, and may be about 3.3 VDC, by way of example. To that end, power supply 80 includes a rectifier 84, such as a half-wave or full-wave diode package, the output of which is filtered by the parallel circuit of a grounded capacitance C1 and grounded 40 KΩ resistance provided by series resistors R1 (30 KΩ) and R2 (10 KΩ), and fed into a regulator 86 which outputs the regulated DC voltage 82 as is conventional. The grounded capacitance C1 includes in parallel a 12 volt zener diode, three 1500 μF electrolytic capacitors, and two 100 μF (all not shown). In accordance with the principles of the present invention, a signal correlated to the AC supply is monitored, which in the embodiment of FIG. 1 is obtained from the junction 87 of resistors R1 and R2 so as to provide an unregulated and filtered DC voltage at 88 generally representative of the AC supply input to transformer 74. Thus, if there is a disruption of AC power, the level of signal 88 will be responsive thereto and will begin to drop.

The unregulated and filtered DC voltage signal at 88 is coupled via an A/D converter 89 to processor 42 which is adapted to monitor the level thereof. Should the voltage signal 88 drop below a level normally indicative of normal power levels, heater unit 16 is adapted to respond thereto so as to avoid drawbacks that might otherwise arise from a disruption in the AC supply. In the embodiment of FIG. 1, a disruption is indicated if the AC supply falls below 93 VAC, which correlates to about 1.0 VDC for the level of signal 88. Thus, processor 42 is adapted to respond to the level of signal 88 falling below 1.0 volt DC by sending a power disruption signal 90 which energizes audible alarm 91 to alert those in the vicinity that heater unit 16 has encountered a power disruption. Additionally, and in order to conserve power so that alarm 91 may be sounded, processor 42 is adapted to discontinue normal operations, including terminating visual displays 92 and suspending energization of heater 46 and/or heater circuits 30, 32, such as setting the states of power control signals 77 and 79 to place relays 76 and 78 in a state to interrupt AC power to the associated power circuits 61, 65 and 69 and/or to terminate control signals 60, 64 and 68 to achieve the same objective. Normal operations may remain suspended until the heater unit 16 is restarted by a user (not shown) who may respond to the alarm 91.

To facilitate operations of processor 42 in response to an AC power disruption, power supply 80 may also be provided with a power storage device such as a 0.47 F super-capacitor 94 coupled to the output 82 of regulator 86. Super-capacitor 94 provides a source of temporary DC energy to power processor 42 and alarm 91 for a period of time, such as at least 15 seconds to one minute. Also, while super-capacitor 94 is shown as being part of power supply 80, it could alternatively be outside thereof as will be readily understood.

Processor 42 may be placed into a sleep mode during which only minimal activities are undertaken so as to conserve power after a disruption in the AC supply. In that regard, processor 42 may suspend all operations except to sound alarm 91 and to monitor signals 82 and 88. In accordance with a further aspect of the present invention, processor 42 may continue to monitor the level of signal 88 to detect restoration of AC power. In that regard, should processor 42 detect that the level of signal 88 again reflects normal power levels, such as by going above 1.0 volt DC, processor 42 may go through a power-up process to be ready for normal operation of heater unit 16 such as directed by an operator (not shown) via user input 54.

Should the power disruption continue, super-capacitor 94 will become depleted to the point where errant operation of controller 40, and particularly processor 42, might occur. To avoid such a situation, additionally or alternatively, regulated DC signal 82 is also coupled to an input of processor 42 by which to monitor the level of signal 82. Super-capacitor 94 will begin to deplete thus dropping the level of signal 82. Should that level go too low to sustain reliable operations on restart, such as below 2.63 volts, processor 42 will completely shut down to thereby completely turn heater unit 16 off. Processor 42 may first initiate a discharge signal 95 to a discharge circuit 96 configured to completely discharge super-capacitor 94 in response to signal 95. Discharge circuit 96 may be a resistive circuit (not shown) coupled between super-capacitor 94 and the output of a logic gate (note shown) adapted to go low or to ground in response to discharge signal 95.

Memory 44 may be a single memory, or may be comprised of multiple memory segments or components, including some aspects within processor 42. In accordance with a yet further aspect of the present invention, at least one aspect 98 of memory 44 (or the entire memory 44) may be non-volatile, in which event processor 42 may, before super-capacitor 94 depletes or discharges, also store into the non-volatile aspect 98 of memory 44 the current operating parameters of heater unit 16 at the time of the AC power disruption. Should power restore as detected by the level of signal 88 before depletion of super-capacitor 94, heater unit 16 may be restored to its pre-disruption operational settings by pulling the settings from the non-volatile memory 98 and placing them into the operating registers and other memory locations, as appropriate, for continued operation of heater unit 16. Additionally, in one embodiment, should power fail altogether, heater unit 16 may be reinitialized when power is restored with the settings prior to the AC disruption. Heater unit 16 may thus be automatically restarted or, alternatively, may be ready to restart upon activation of a user input 54 after an operator (not shown) confirms that the settings such as may be shown on displays 92 are acceptable.

Advantageously, processor 42 is adapted to avoid taking AC ripple as an AC disruption so as not to unnecessarily respond as if an AC disruption had occurred. An exemplary AC disruption detection process 100 addressing that concern will be described with reference to FIG. 2. To that end, at step 102 processor 42 obtains a reading from A/D converter 89 indicative of the level of unregulated and filtered DC voltage 88. An AC disruption threshold level stored in memory 44 represents a DC voltage level at or below which an AC disruption is assumed to have occurred. In the embodiment shown, an AC supply below 93 VAC is selected, which translates to an AC disruption threshold level of 1.0 VDC. At step 104, the reading from converter 89 is compared to that AC disruption threshold level.

If, at step 104, the level of voltage 88 is above the threshold, then it is assumed that no AC disruption has occurred, and the process will loop back to step 102 to again take a reading from A/D converter 89. Alternatively, process 100 may end until a program operating within processor 42 subsequently initiates process 100 anew. If, however, at step 104, the level of voltage 88 is at or below the threshold, a wait step at 105 is undertaken, such as of about 0.5 seconds (such as between about 300 milliseconds and 650 milliseconds), and another reading from A/D converter 89 is taken to get a new sample of the level of voltage 88 at step 106. A comparison thereof to the threshold is undertaken at step 108, and if the level is above the threshold, then it is assumed that what was possibly an AC disruption at step 104 may have been due to AC ripple, and the process loops back to step 102 to start over (or ends until processor 42 later reinitiates process 100). However, if the result of the comparison at step 108 again reveals a voltage level 88 below the threshold, then it is concluded that there has been an AC disruption and the necessary procedures are undertaken based thereon at step 110, such as storing the current operational parameters of heater unit 16 into the non-volatile aspects 98 of memory 44 for later use (if processor 42 is so-adapted), shutting down the heaters 46, 30 and 32 and the displays 92, and initiating alarm 91, after which processor 42 may be placed into a sleep mode.

Processor 42 may include a single microprocessor or other computer or programmable logic device. Alternatively, and as will discussed with reference to FIG. 3, processor 42 may be defined by redundant CPUs, such as a main CPU 120 and an auxiliary CPU 122 communicating via a CPU serial peripheral interface 124, and may include a hardware watchdog 125 and software watchdog functionality, all as described in concurrently-filed U.S. patent application Ser. No. 11/927,054 the disclosure of which is incorporated herein by reference in its entirety. Main CPU 120 is adapted to operate as the primary processor of controller 40 and handle user interface tasks, temperature measurement, communication and debugging capabilities, and control of heaters 46, 30, and 32. Main CPU 120 may also handle calibration of temperature measurement circuitry as described in aforementioned U.S. patent application Ser. No. 11/927,000. Auxiliary CPU 122 is adapted to operate as an auxiliary processor of controller 40 and handle back-up failure management for heater circuits 30 and 32 such as via control of relay 78, and displays 92 (which may be LED and/or other visually perceptible display elements and drivers), and responsibilities such as verifying that the proper heated breathing circuit is being used as described in aforementioned U.S. patent application Ser. No. 11/927, 004. Main CPU 120 and auxiliary CPU 122 thus operate in conjunction with hardware watchdog 125 to provide redundant power control for heaters 46, 30 and 32 as described in aforementioned U.S. patent application Ser. No. 11/927,054.

Figure 3:
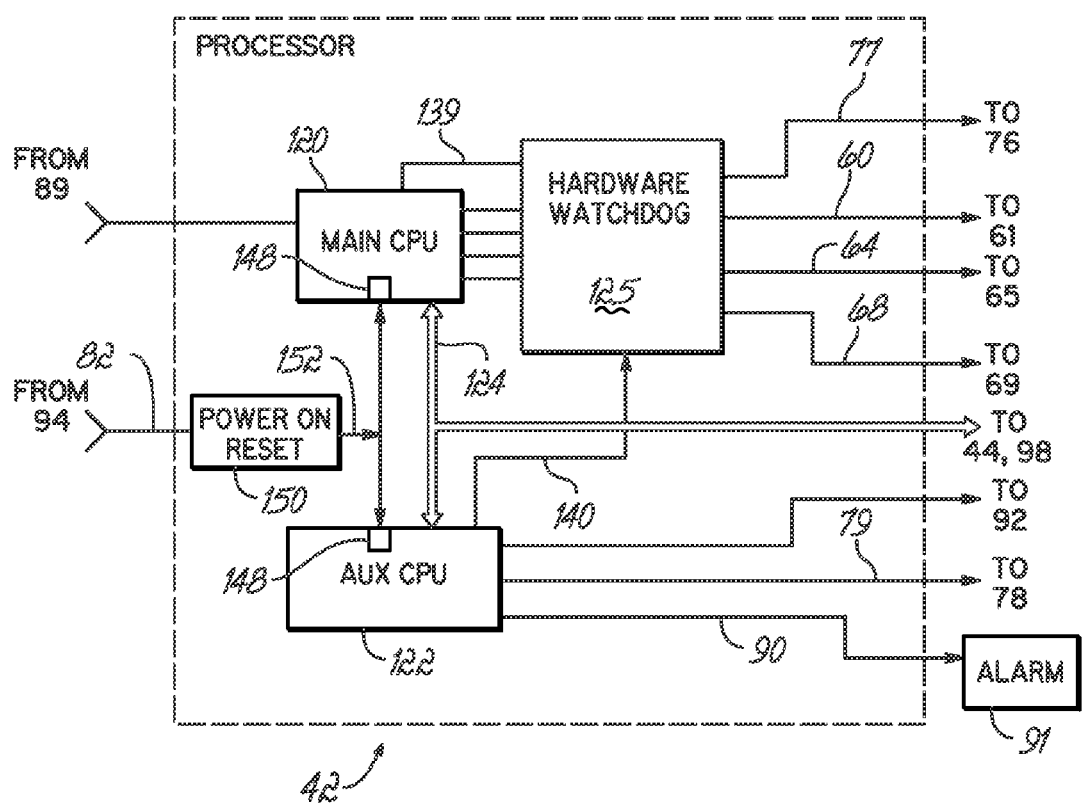
FIG. 3 is a block diagram of an alternative embodiment of the processor of the heater unit of FIG. 1.

Main CPU 120 is adapted to monitor the level of signal 88 such as by taking the readings from A/D converter 89. Main CPU 120 may perform the AC disruption detection process 100 as described with reference to FIG. 2 above, and at step 110 may directly control alarm 91 such as with power disruption signal 90 therefrom. Alternatively, at step 110, main CPU 120 may output instructions over interface 124 to auxiliary CPU 122 for the latter to initiate the power disruption signal 90 as indicated in FIG. 3. In addition to thus controlling alarm 91, auxiliary CPU 122 may be adapted to control indicators of the power status of heater unit 16 in response to instructions from main CPU 120. To that end, auxiliary CPU 122 may be adapted to normally generate a power stable signal (not shown) which illuminates a green LED or green portion of dual color LED (both not shown) indicating that heater unit 16 is turned on and operating. In response to the instructions from main CPU 120 resulting in generation of the power disruption signal 90 by auxiliary CPU 122, the power stable signal will terminate such that the green LED (or portion) will extinguish and, instead, a differently colored LED (such as a red LED or red portion of the dual color LED) may be illuminated.

In one embodiment, at the beginning of the wait step 105 of FIG. 2, the green LED (or portion) may be extinguished and another colored LED (such as a yellow LED or a yellow portion of a multi-color LED) illuminated in anticipation of a potential conclusion of an AC disruption. About 300 milliseconds into the wait of step 105, an event could be logged into non-volatile memory 98. Thereafter, at step 108, if the comparison results in the level being above the threshold, then the yellow LED (or portion) will extinguish and the green LED (or portion) re-illuminated, and the event previously logged in memory 98 may be deleted. If, however, the result of the comparison at step 108 is to conclude that there is an AC disruption, the yellow LED (or portion) will be extinguished and instead the red LED (or portion) will be illuminated, the event will remain stored, and the other AC disruption procedures will continue at step 10, such as sounding the alarm and/or storing operational parameters.

In one embodiment, in response to detection of the AC disruption, such as at step 110 of the process 100 of FIG. 2, processor 42 may undertake a power down process 130 as will be described with reference to FIG. 4. To that end, at step 132, the current operational parameters of heater unit 16 (such as such as operation settings, calibration data, and logs) are loaded, such as over interface 124 which may also communicate, directly or through an I/O device (not shown) with memory 44, into non-volatile aspects 98 of memory 44 for later use such as to return heater unit 16, after cessation of the AC disruption or on power restore, to its previous operating state. As process 130 is being undertaken in circumstances where there has been an AC disruption, power could be quickly lost. Hence, where main CPU and auxiliary CPU 122 are provided, the operational parameters for main CPU 120 may be stored first, and then the operational parameters of auxiliary CPU 122 then stored, to thereby first undertake to ensure that the critical operations of heater unit 16 by main CPU 120 are stored. To that end, after operating parameters from main CPU 120 are stored, main CPU 120 then issues a command to auxiliary CPU 122 across the CPU serial peripheral interface 124 for auxiliary CPU 122 to load its operating parameters into memory 98.

After storing the operational parameters at step 132, or skipping step 132 if heater unit 16 is not adapted to store such parameters, process 130 continues to step 134 whereat the displays 92 are displayed, to step 136 whereat operation of heaters 46, 30 and 32 is suspended as previously described, and to step 138 whereat watchdog 125 is disabled such as by signal 139 from main CPU 120 and/or signal 140 from auxiliary CPU 122 as explained in the aforementioned U.S. patent application Ser. No. 11/927,054. While shown in that sequence in FIG. 4, steps 134, 136 and 138 could be done in different or mixed sequences. Then, at step 142, the power disruption signal 90 is generated to energize alarm 91 so as to audibly alert those in the area to the AC disruption. Step 142 could be undertaken before or between any of steps 134, 136 and 138, if desired. Finally, at step 144, main CPU 120 and auxiliary CPU 122 are placed into the sleep mode.

In the sleep mode, operations thereof are discontinued, but alarm 91 may continue to be energized such as by an amplifier and/or flip-flop (not shown) powered by the DC signal 82 for so long as there is power therefrom (such as until supercapacitor 94 is discharged as explained above). Main CPU and auxiliary CPU 122 may be of the type which have a reset input 148 responsive to which the CPU's will shut down completely. For that purpose, processor 42 includes a power-on reset circuit or processor 150 which is powered directly by signal 82. Power-on reset circuit 150 may be a commercially available microprocessor supervisory circuits. Such circuits are designed to operate at extremely low DC voltage levels and are programmed to output a reset signal 152 when the operating level falls to a predetermined level. In the embodiment shown herein, reset circuit 150 is programmed to generate the reset signal 152 if the level of regulated DC voltage 82 goes below a safe operating threshold, such as 2.63 VDC, at which the DC supply of signal 82 is deemed too low to sustain reliable operations of main CPU 120 and/or auxiliary CPU 122. Reset signal 152 is coupled to the reset inputs 148 of CPU's 120 and 122 to cause them to shutdown when the level of signal 82 drops below the safe operating threshold. The reset signal 152 may also be used as the signal 96 to drive discharge circuit 154 to discharge super-capacitor 94 and thus silence alarm 91 and terminate any remaining electrical functions of heater unit 16. Although shown as a separate circuit, the functionality of circuit 150 could be programmed into one of CPU's 120 and 122 to cause shut down of the CPU's such as first instructing the other CPU to shut down (over interface 124) and then causing itself to shut down. Additionally or alternatively, the reset signal 152 may be initiated in response to a depression of a button (not shown) at user input 54 which will also silence alarm 91.

Prior to complete shutdown, if the AC disruption is terminated, the level of signal 88 will rise above the 1.0 VDC level which previously indicated that there was such a disruption. Processor 42 is adapted to monitor same in the sleep mode and will initiate a reactivation sequence 180 should that occur as will now be described with reference to FIG. 5. Process 180 begins at step 182 in response to detection that the AC disruption has ended at which processor 42 is to come back out of the sleep mode and into a normal operation mode. In that step, main CPU 120 may be first restored and then auxiliary CPU 122 restored such as by a command from main CPU 120 over interface 124. At step 184, the parameters which had been stored in memory 98 at step 132 of process 130 (FIG. 4) are retrieved to restore processor 42 to its pre-disruption condition. Where the processor 42 of FIG. 3 is involved, main CPU 120 retrieves its parameters first, and then sends a command via interface 124 to the auxiliary CPU 122 to retrieve its parameters. At step 186, watchdog 125 is enabled by restoration of signal 138 and/or signal 139 as described in aforementioned U.S. patent application Ser. No. 11/927,054. At step 188 signal 90 is terminated to thus shut off alarm 91. The process continues to step 190 to enable displays 92, which may occur by auxiliary CPU 122 responding to a command from main CPU 120. Alternatively, or additionally, process 180 may wait after step 190 for a user to check the operating parameters, such as via displays 92, and to indicate that operation may resume such as by activation of a button (not shown) of user input 54. Step 192 follows step 190, or the activation previously mentioned, at which the heaters 46, 30 and 32 are re-energized for operation such as by activating relays 76 and 78. Process 180 then ends with processor 42 again operation in accordance with the normal programming to generate control signals 60, 64, and 68 to regulate the heaters.

In use, heater unit 16 is operating to regulate heaters 46, 30 and 32. In the event of an AC disruption, processor 42 will cause alarm 91 to sound and may go into a sleep mode. The operating parameters may also be stored in non-volatile memory 98. If the AC disruption is terminated while there is still a level of DC power sufficient to reliably operate processor 42, the stored operating parameters may be recalled to restore processor 42 to its operating condition prior to the AC disruption. If the level of DC power drops too low before the AC disruption is terminated, the processor 42 may be shut down completely.

By virtue of the foregoing, there is thus provided a heater unit adapted to overcome drawbacks which might otherwise result from power disruptions. While the invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. By way of example, while the embodiments have been described in relation to a disruption in an AC source of supply, the principles of the present invention apply where the heater unit 16 is to be powered from an external DC source of supply. Further, while heater unit 16 is shown as part of a ventilator driven respiratory system, 10, it will be appreciated that heater unit 16 could be employed in other respiratory systems such as where the gas is supplied from a hospital oxygen supply, or in combination with a CPAP or BiPAP pump, or other air or oxygen pumping system. Also, should the level of reading taken from A/D converter 89 exceed an upper threshold, which indicates a high AC condition that is not desirable, heater unit 16 may be adapted to shut down as in the case of an AC disruption as above-described. Thus, the invention in its broader aspects is therefore not limited to the specific details, representative apparatus and methods and illustrative examples shown and described. Accordingly, departures may be made from such details without departing from the scope or spirit of Applicants' general inventive concept.

Having described the invention, what is claimed is:

1. In a humidification system comprising a heater unit configured to heat liquid contained within a chamber supported by the heater unit, the chamber adapted to couple to a source of breathable gas via a gas conduit and to a patient via an inspiratory limb so as to impart heat to a portion of a respiratory system, the heater unit being independent of said source of breathable gas, the heater unit including an audible alarm and heater thermally couplable to said chamber and adapted to be selectively energized from a source of electrical supply, a method of power failure management for the heater unit comprising:

monitoring the source of electrical supply at the heater until for a disruption;

in response to detection of the disruption of, sounding an audible alarm of the heater unit.

2. The method of claim 1 further comprising suspending energization of the heater in response to detection of the disruption.

3. The method of claim 1 wherein the heater unit includes operating parameters, the method further comprising storing the operating parameters in a non-volatile memory in response to detection of the disruption.

4. The method of claim 3 further comprising monitoring for termination of the disruption, and recalling the operating parameters from the non-volatile memory in response to detection of termination of the disruption.

5. The method of claim 1 wherein the heater unit includes electronic components and a power supply adapted to provide a regulated DC voltage from the source of electrical supply to power the electronic components, the method further comprising drawing power from a power storage device operatively associated with the power supply in response to detection of the disruption.

6. The method of claim 5 wherein the heater unit includes a processor, the method comprising the processor entering a sleep mode in response to detection of the disruption.

7. The method of claim 6 further comprising shutting down the processor in response to a level of the power storage device being below a level to sustain reliable operation of the processor.

8. The method of claim 6 wherein the heater unit includes operating parameters for the processor, the method further comprising storing the operating parameters in a non-volatile memory in response to detection of the disruption.

9. The method of claim 8 further comprising monitoring for termination of the disruption, and recalling the operating parameters from the non-volatile memory in response to detection of termination of the disruption.

10. The method of claim 1 wherein the heater unit includes a processor, the method comprising the processor entering a sleep mode in response to detection of the disruption.

11. The method of claim 10 further comprising shutting down the processor in response to the disruption being sufficient to interfere with reliable operation of the processor.

12. The method of claim 1 wherein the source of electrical supply is an AC supply, monitoring the source of electrical supply including generating a variable DC voltage signal correlated to the AC supply whereby to detect that there is a disruption in the AC supply in response to the variable DC voltage falling below a predetermined threshold.

13. The method of claim 12 further comprising detecting that there is a in the AC supply in response to the DC variable voltage falling below the predetermined threshold at a first time and the DC variable voltage still being below the predetermined threshold at a second, subsequent time.

14. The method of claim 1, the heater unit including a visual display, the method further comprising disabling the visual display in response to detection of the disruption.

15. A humidification system comprising:
a heater unit configured to heat liquid contained within a chamber supported by the heater unit, said chamber adapted to couple to a source of breathable gas via a gas conduit and to a patient via an inspiratory limb so as to impart heat to a portion of a respiratory system, the heater unit being independent of said source of breathable gas, the heating unit including:
a heater thermally couplable to said chamber;
a power supply coupled to a source of electrical supply and adapted to output a regulated DC supply;
electronic circuitry adapted to be energized from the regulated DC supply, the heater responsive to the electronic circuitry whereby to be selectively energized from the source of electrical supply, the electronic circuitry being responsive to disruption of the source of electrical supply to output a power disruption signal; and
an alarm responsive to the power disruption signal to generate an audible alarm whereby to provide an alert indicative of the disruption.

16. The humidification system of claim 15, wherein the electrical supply is an AC supply, the power supply further adapted to output a variable DC voltage correlated to a level of the AC supply, the electronic circuitry being responsive to a drop in the variable DC voltage indicative of disruption of the source of electrical supply to output the power disruption signal.

17. The humidification system of claim 16, the heater unit further comprising a power storage device coupled to the regulated DC supply, whereby to temporarily provide power after disruption of the AC supply.

18. The humidification system of claim 17, the power storage device being a super-capacitor.

19. The humidification system of claim 17, the heater unit further comprising a non-volatile memory, the electronic circuitry being responsive to the disruption to store operating parameters in the non-volatile m memory.

20. The humidification system of claim 19, the electronic circuitry being responsive to termination of the disruption to restore the operating parameters from the non-volatile memory.

21. The humidification system of claim 15, the electronic circuitry being responsive to the disruption to suspend energization of the heater.

22. The humidification system of claim 15, the electronic circuitry including a processor adapted to monitor the source of electrical supply and to output the power discharge signal in response to the disruption.

23. The humidification system of claim 22, the processor adapted to power down into a sleep mode in response to the disruption.

24. The humidification system of claim 23, the processor adapted to shut down in response to disruption of the source of electrical supply below a level to provide reliable operation of the processor.

25. The humidification system of claim 22, the heater unit further comprising a power storage device coupled to the regulated DC supply, whereby to temporarily provide power after disruption of the AC supply.

26. The humidification system of claim 25, the power storage device being a super-capacitor.

27. The humidification system of claim 25, the heater unit further comprising a non-volatile memory, the processor having operating parameters, the processor being responsive to the disruption to store the operating parameters in the non-volatile m memory.

28. The humidification system of claim 27, the processor being responsive to termination of the disruption to restore the operating parameters from the non-volatile memory.

29. The humidification system of claim 15, the heater unit further comprising a visual display, the electronic circuitry being responsive to detection of the disruption to disabling the visual display.

* * * * *

UNITED STATES PATENT AND TRADEMARK OFFICE
CERTIFICATE OF CORRECTION

PATENT NO. : 7,777,635 B2  Page 1 of 1
APPLICATION NO. : 11/927068
DATED : August 17, 2010
INVENTOR(S) : Zhan Liu, Ashok Mahadevan and Robert L. Snyder It is certified that error appears in the above-identified patent and that said Letters Patent is hereby corrected as shown below:

Column 3
Line approximately 17, "FIG. 2 is flowchart" should be -- FIG. 2 is a flowchart --

Column 4
Line approximately 13, "responsive devices such as" should be -- responsive device such as a --

Column 7
Line approximately 19, "will discussed" should be -- will be discussed --

Column 8
Line approximately 20-21, "(such as such as operation" should be -- (such as operation --

Column 9
Line approximately 51, "again operation" should be -- again operating --

Claim 1
Column 10, line 39, "until for a" should be -- unit for a --

Claim 13
Column 11, line 22, "there is a in the AC" should be -- there is a disruption in the AC --

Claim 19
Column 12, line 14, "non-volatile m memory" should be -- non-volatile memory --

Claim 27
Column 12, line 43, "volatile m memory" should be -- volatile memory --

Claim 29
Column 12, lines 49-50, "disruption to disabling" should be -- disruption to disable --

Signed and Sealed this

Sixteenth Day of November, 2010

David J. Kappos
*Director of the United States Patent and Trademark Office*